United States Patent
Josic et al.

(10) Patent No.: US 7,166,709 B2
(45) Date of Patent: Jan. 23, 2007

(54) HAEMOSTATICALLY ACTIVE PREPARATION CONTAINING VWF AND METHOD FOR THE PRODUCTION THEREOF

(75) Inventors: Djuro Josic, Vienna (AT); Monika Stadler, Wienerherberg (AT); Gerhard Gruber, Vienna (AT)

(73) Assignee: Octapharma AG, Lachen (CH)

( * ) Notice: Subject to any disclaimer, the term of this patent is extended or adjusted under 35 U.S.C. 154(b) by 188 days.

(21) Appl. No.: 10/257,375

(22) PCT Filed: Apr. 4, 2001

(86) PCT No.: PCT/EP01/03819

§ 371 (c)(1),
(2), (4) Date: Oct. 17, 2002

(87) PCT Pub. No.: WO01/79260

PCT Pub. Date: Oct. 25, 2001

(65) Prior Publication Data

US 2003/0138913 A1  Jul. 24, 2003

(30) Foreign Application Priority Data

Apr. 18, 2000 (EP) .................. 00108430

(51) Int. Cl.
A23J 1/00 (2006.01)
A61K 35/14 (2006.01)
C07K 1/00 (2006.01)

(52) U.S. Cl. .................. 530/412; 530/383; 530/384

(58) Field of Classification Search ............... 530/383, 530/384, 412; 514/12, 2; 435/68.1, 69.9; 424/101

See application file for complete search history.

(56) References Cited

U.S. PATENT DOCUMENTS

| 5,252,709 A | 10/1993 | Burnouf et al. |
| 5,408,039 A * | 4/1995 | Burnouf-Radosevich et al. 530/383 |
| 5,639,730 A * | 6/1997 | Eibl et al. ..................... 514/21 |
| 6,005,077 A * | 12/1999 | Schwarz et al. ............ 530/383 |

FOREIGN PATENT DOCUMENTS

| EP | 0 367 840 | 5/1990 |
| EP | 0 774 261 A2 | 11/1996 |
| EP | 0 934 748 A2 | 12/1998 |
| WO | WO 93/15105 | 8/1993 |

OTHER PUBLICATIONS

Mazurier et al., "Developement preclinique du concentre de facteur Willebrand vWF SD-35-dh", Sang Thrombose Vaisseaux, vol. 11, No. Spezial, (Oct. 1999), XP-000925923, pp. 30-35.

* cited by examiner

Primary Examiner—Jon Weber
Assistant Examiner—Robert B. Mondesi
(74) Attorney, Agent, or Firm—Jacobson Holman PLLC

(57) ABSTRACT

A process for preparing a hemostatically active preparation containing von Willebrand factor (vWF) from a fraction of human plasma by chromatographic purification of a vWF-containing plasma fraction on an anion-exchange material which has the anion-exchanging groups on grafted polymeric structures (tentacle materials), collecting a vWF-containing fraction, followed by purification of said fraction using gel permeation to prepare a purified thermally stable vWF-containing preparation; and heating the preparation for inactivating viruses.

7 Claims, 1 Drawing Sheet

HAEMOSTATICALLY ACTIVE PREPARATION CONTAINING VWF AND METHOD FOR THE PRODUCTION THEREOF

This is a nationalization of PCT/EP01/03819, filed Apr. 4, 2001 and published in German.

The present invention relates to a process for preparing a virus-inactivated hemostatically active preparation containing von Willebrand factor (vWF) from a fraction of human plasma, and to a hemostatically active vWF-containing preparation obtainable by the process according to the invention.

The von Willebrand disease is a blood coagulation disorder which, unlike in hemophilia A or B, manifests itself as bleedings in soft tissues, especially mucosae. Deficiency in the so-called von Willebrand factor (vWF) was recognized to be the cause of this disease. To date, this factor has been administered to the patients through factor VIII preparations in which vWF is also contained, but often only in an unsatisfactory quality and unsatisfactory amount. Although the preparation of vWF by genetic engineering has been successful, there is still an urgent need for applying improved purification methods for preparing vWF from donor blood or plasma.

In EP-A-0 934 748, a highly pure vWF having a content of at least 15% vWF multimers, which consist of 13 or more protomers (HMW-VWF multimers), is described. It is obtained by a multistep chromatographic purification, wherein gel filtration in a group separation mode can be initially performed instead of cryoprecipitation. To inactivate viruses, for example, treatment with solvents and detergents and heat treatment in a lyophilized state for 72 h at 80° C. has been described.

Josic et al., "Purification of factor VIII and vWF factor from human plasma by anion-exchange chromatography", Journal of Chromatography B, 662 (1994), 181–190 and Schwinn et al., "A Solvent/detergent Treated, Pasteurized and Highly Purified Factor VIII Concentrate", Arzneimittel-Forschung 1 Drug Research 44 (1), 2, 188–191 (1994), relate to the purification of a factor VIII/vWF complex, effecting purification through an ion-exchange material and performing two independent steps for the inactivation of viruses. Treatment with solvent/detergent and pasteurization (10 h at 63° C.) in the presence of stabilizers is effected. Although factor VIII is hardly denatured by the pasteurization (95% residual activity), the vWF is changed in its activity and multimer distribution (85% residual antigen), and a loss of high-molecular weight multimers occurs, resulting in a vWF antigen to activity ratio of 2.2 (activity to antigen=0.5).

U.S. Pat. No. 5,714,590 describes the purification of a factor VIII complex by ion-exchange chromatography. Thus, an EMD-TMAE-Fractogel column material is employed which is also used for gel permeation. For virus inactivation, a treatment with solvent/detergent is proposed. Heat treatment is not described. The product obtained also contains vWF, only the vWF antigenicity being stated.

The object of the invention is to provide a novel process for the purification of vWF from human plasma. Such process is to yield vWF in an improved quality and effectiveness.

The object of the invention is achieved by a process for preparing a hemostatically active preparation containing von Willebrand factor (vWF) from a fraction of human plasma, characterized in that a chromatographic purification of a vWF-containing plasma fraction on an anion-exchange material which has the anion-exchanging groups on grafted polymeric structures (tentacle materials) is performed, a vWF-containing fraction is collected, followed by purification of the fraction using gel permeation, and the preparation is heated for inactivating viruses. The tentacle materials which can be employed in the process according to the invention are disclosed, in particular, in EP-A-0 337 144. This publication is included herein by reference. Said materials are preferably polyacrylamide tentacle polymers grafted to diols of Fractogel® as supplied by Merck, Darmstadt, Germany.

Figure 1:
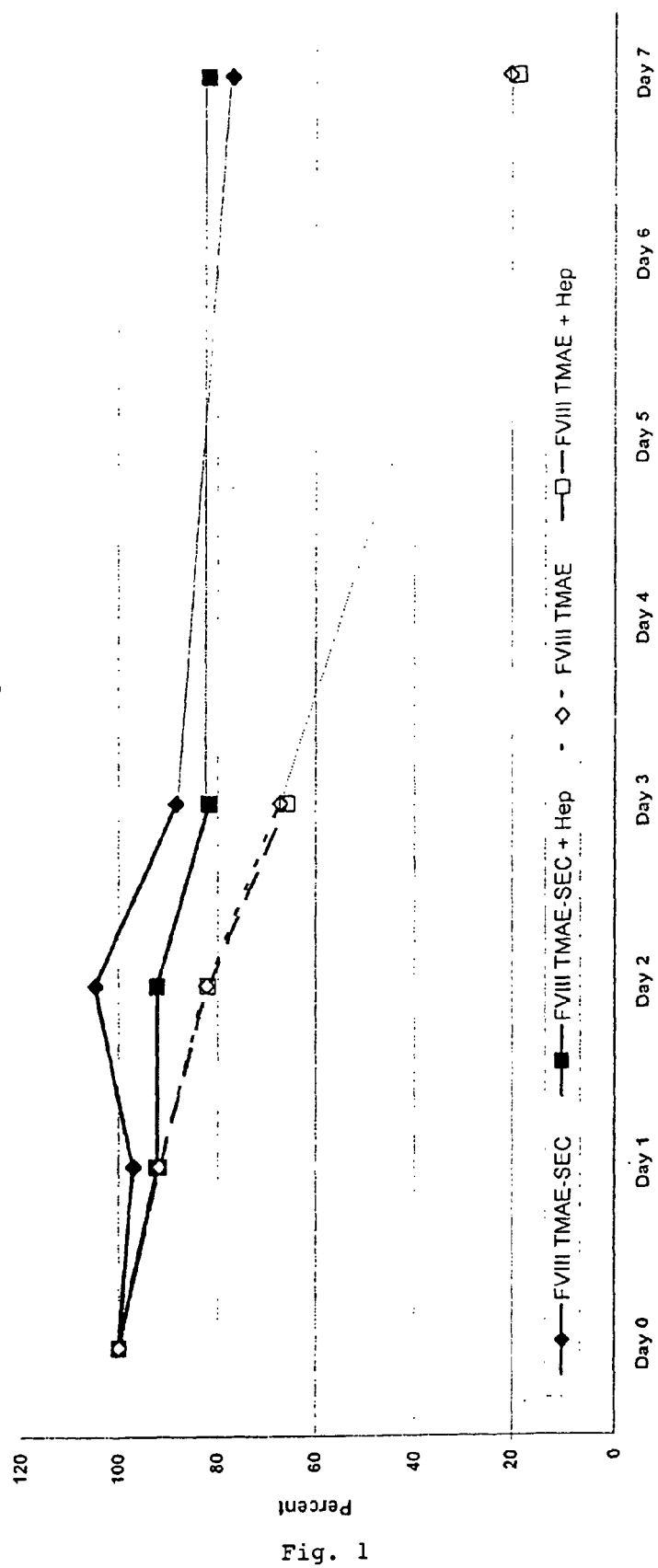
FIG. 1 shows the stability of the product obtainable according to the invention as compared to the products purified solely by anion-exchange chromatography.

In obtaining the results recorded in FIG. 1, FVIII concentrates were reconstituted in Aqua ad inj. and Aqua ad inj. containing 5 IU Heparin/ml, respectively. After transfer into infusion bags samples were stored at room temperature. At time points indicated samples were drawn and examined for FVIII:C activity (chromogenic). FVIII recovery is expressed in percentage of initial activity.

This procedure surprisingly results in a product having a high vWF content as compared to F VIII. Due to the gel permeation step, the sequence according to the invention results in the removal of inter-α-trypsin inhibitor as well as other factors which may have contributed to a reduction of the quality of the product in known preparation methods. The sequence of chromatographic steps according to the invention yields a vWF preparation which is surprisingly stable. Surprisingly, the vWF fraction obtainable using the method according to the invention is essentially stable in an aqueous solution at room temperature for extended periods of time (measurement was effected for up to one week). In addition, the preparation according to the invention contains the vWF in a native form and free from fragments.

Preferably, the thermally stable preparation and the heated preparation exhibit only one peak in HPLC gel filtration analysis.

Especially, the thermally stable preparation can be heated at a temperature of more than 80° C. in a lyophilized state according to the process. In another embodiment of the process according to the invention, the preparation is heated at a temperature of more than 90° C., especially at 100° C. According to the invention, the heating is preferably effected for a period of time of at least 1 h up to 5 h, especially from 2 to 3 h. Thus, all transfusion-relevant viruses, especially non-lipid-coated viruses, such as parvoviruses or hepatitis A viruses, are inactivated. Astonishingly, the product obtainable according to the invention withstands this demanding heat treatment without a substantial loss in activity.

According to the invention, purification of the vWF-containing fraction can be additionally effected by at least one adsorption- and/or affinity-chromatographic treatment.

According to the invention, a vWF-containing fraction which is obtained from pooled human plasma and can be purified by the process according to the invention may also be used.

The present invention also relates to a hemostatically active vWF-containing preparation obtainable by the process according to the invention.

The preparation according to the invention is free from infectious blood-borne viruses, especially HIV, HBV, HCV, HAV and parvoviruses.

Especially, the preparation according to the invention contains vWF in a high-molecular weight form which shows a minimum of 13 to 16 multimer bands upon electrophoretic analysis. The number of multimers and their distribution pattern is a measure of the similarity of a vWF preparation with native vWF in plasma. Further, the ratio of ristocitin cofactor as a surrogate marker for vWF activity to vWF antigen in the preparation according to the invention is at least 0.8. This is another measure of the integrity of the vWF molecule.

The preparation according to the invention preferably further contains factor VIII in a native form. The use of complexes of F VIII and vWF for treating the von Willebrand disease has proven particularly useful in clinical use.

Further, the following proteins were removed from the preparation according to the invention down to below an immunochemical detection limit: immunoglobulins, fibrinogen, fibronectin, and inter-α-trypsin inhibitor. This is presumably the reason for the extraordinary stability of the product according to the invention.

The invention will be further illustrated by the following Examples.

EXAMPLES

About 47 kg of cryoprecipitate is treated with 15% (w/w) of a 2% (w/w) aluminum hydroxide solution. After centrifugation, the sample is virus-inactivated with 0.30% TnBP/1% Triton X 100. Oil extraction is followed by anion-exchange chromatography on Fractogel EMD TMAE (tentacle gel supplied by Merck, Darmstadt, Germany).

The buffer conditions are as follows:
Buffer AM, first washing step:
120 mM NaCl, 10 mM Na citrate, 120 mM glycine, 1 mM $CaCl_2$, pH 6.9–7.1; osmolality: 360–400 mosmol/kg.
Buffer BM, second washing step:
235 mM NaCl, 10 mM Na citrate, 120 mM glycine, 1 mM $CaCl_2$, pH 6.9–7.1; osmolality: 570–610 mosmol/kg.
Buffer CM, elution:
700 mM NaCl, 10 mM Na citrate, 120 mM glycine, 1 mM $CaCl_2$, pH 6.9–7.1; osmolality: 1380–1480 mosmol/kg.
Buffer DM, third washing step:
1.5 M NaCl.

The fractions showing vWF/FVIII activity are subjected to size exclusion chromatography on Fractogel EMD Bio SEC (gel supplied by Merck, Darmstadt, Germany). After ultra-/diafiltration, formulation is effected with the following composition: 400 mM NaCl, 10 mM Na citrate, 1 mM $CaCl_2$, 133 mM glycine, 1% sucrose.

This is followed by sterile filtration. The preparation is filled into vials and lyophilized, followed by a heat treatment at a temperature of 100° C. The heat treatment takes 120 minutes.

FIG. 1 shows the stability of the product obtainable according to the invention as compared to the products purified solely by anion-exchange chromatography. After the anion-exchange chromatography, the product according to the invention was treated with size-exclusion chromatography. It is found that the product according to the invention had still an activity of 80% upon storage with or without heparin in an aqueous solution at room temperature, while products which had not experienced size-exclusion chromatography exhibited an activity of only 20% after 7 days.

The invention claimed is:

1. A process for preparing a hemostatically active preparation containing von Willebrand factor (vWF) from a fraction of human plasma by
   a) chromatographic purification of a vWF-containing plasma fraction on an anion-exchange material which has the anion-exchanging groups on grafted polymeric structures (tentacle materials), collecting a vWF-containing fraction, characterized in that
   b) purification of said fraction using gel permeation to prepare a purified thermally stable vWF-containing preparation follows, and
   c) heating the preparation for 1–5 hours (h) at a temperature of more than 80° C. in a lyophilized state for inactivating viruses and is stable in an aqueous solution at room temperature for at least one week.

2. The process according to claim 1, characterized in that the thermally stable preparation and the heated preparation exhibit only one peak in HPLC gel filtration analysis.

3. The process according to claim 1, characterized in that the preparation is heated at a temperature of more than 90° C.

4. The process according to claim 1, characterized in that the preparation is heated at a temperature of 100° C.

5. The process according to claim 1, characterized in that the preparation is heated for 2–3 h.

6. The process according to claim 1, characterized in that said purification by gel permeation is effective as a final measure for protein purification.

7. The process according to claim 1, characterized in that said fraction is purified from pooled human plasma.

* * * * *